(12) United States Patent
Kao

(10) Patent No.: US 6,558,945 B1
(45) Date of Patent: May 6, 2003

(54) METHOD AND DEVICE FOR RAPID COLOR DETECTION

(75) Inventor: Pin Kao, Fremont, CA (US)

(73) Assignee: Aclara Biosciences, Inc., Mountain View, CA (US)

(*) Notice: Subject to any disclaimer, the term of this patent is extended or adjusted under 35 U.S.C. 154(b) by 0 days.

(21) Appl. No.: 09/520,423

(22) Filed: Mar. 8, 2000

Related U.S. Application Data

(60) Provisional application No. 60/123,349, filed on Mar. 8, 1999.

(51) Int. Cl.[7] .............................. C12M 1/34; C12Q 1/68; C12P 19/34; G01N 33/00; C07H 21/02
(52) U.S. Cl. ........................ 435/287.2; 435/6; 435/91.1; 435/287.1; 436/94; 536/23.1
(58) Field of Search ........................ 435/6, 91.1, 183, 435/283.1, 287.1, 287.2; 436/94; 536/23.1, 24.3, 24.33, 25.3; 422/82.05, 82.07, 82.08

(56) References Cited

U.S. PATENT DOCUMENTS

| | | |
|---|---|---|
| 4,820,048 A | 4/1989 | Barnard |
| 5,126,022 A | 6/1992 | Soane et al. |
| 5,543,026 A | 8/1996 | Hoff et al. |
| 5,570,015 A | 10/1996 | Takaishi et al. |
| 5,571,410 A | 11/1996 | Swedberg et al. |
| 5,587,128 A | 12/1996 | Wilding et al. |
| 5,630,924 A | 5/1997 | Fuchs et al. |
| 5,741,411 A | 4/1998 | Yeung et al. |
| 5,776,782 A | 7/1998 | Tsuji |
| 5,777,733 A | 7/1998 | Radziuk |
| 5,846,708 A | 12/1998 | Hollis et al. |
| 5,948,227 A * | 9/1999 | Dubrow ............... 204/455 |

OTHER PUBLICATIONS

Quesada et al., Multiple capillary DNa sequencer that uses fiber–optic illumination and detection. Electrophoresis 17, 1841–1851, 1996, Dec. 1996.*
Tang et al., A high–sensitivity CCD system for parallel electron energy–loss spectroscopy (CCD for EELS) 175, 100–107, 1994, Aug. 1994.*
Moleculae Probes Catalog (1996, sixth edition), p. 34, 206, and 267. Published by Molecular Probes, Inc., 4849 Pitchford Avenue, Eugene, OR 97402–9165, USA, 1996.*
Huang, C. et al. (1992). "DNA Sequencing Using Capillary Array Electrophoresis," *Analytical Chemistry* 64:2149–2154.
Khandurina, J. et al. (1999). "Microfabricated Porous Membrane Structure for Sample Concentration and Electrophoretic Analysis," Analytical Chemistry 71(9):1815–1819.
Kheterpal, I. et al. (1996). "DNA Sequencing Using a Four–Color Confocal Fluorescence Capillary Array Scanner," *Electrophoresis* 17:1852–1859.
Takahashi, S. et al. (1994). "Multiple Sheath–Flow Gel Capillary–Array Electrophoresis for Multicolor Fluorescent DNA Detection," *Analytical Chemistry* 66(7):1021–1026.
Woolley, A.T. et al. (1994). "Ulta–High–Speed Fragment Separations Using Microfabricated Capillary Electrophoresis Chips," *PNAS USA, Biophysics* 91(24):11348–11352.

* cited by examiner

*Primary Examiner*—Ethan C. Whisenant
*Assistant Examiner*—Frank Lu
(74) *Attorney, Agent, or Firm*—Morrison & Foerster LLP

(57) ABSTRACT

Methods and apparatus are provided for miniaturized DNA sequencing using four-color detection. The method employs a multichannel chip where the channels are simultaneously irradiated to excite fluorophores in the channels. The emitted light is divided into four different wavelength beams and read by CCDs.

The results are multiplexed for rapid sequencing of a large number of samples, with high fidelity of the sequences.

17 Claims, 3 Drawing Sheets

METHOD AND DEVICE FOR RAPID COLOR DETECTION

CROSS-REFERENCE TO RELATED APPLICATIONS

This application claims priority of U.S. Patent Provisional Application Serial No. 60/123,349 filed on Mar. 8, 1999, which disclosure is incorporated herein by reference.

INTRODUCTION

1. Technical field

The field of this invention is electrophoretic nucleic acid sequencing.

2. Background

Microfluidic devices offer numerous opportunities for rapid manipulations of small volumes. With the ability to move small volumes rapidly from one site to another and perform reactions in very small volumes, where the rate of reaction is greatly enhanced, the opportunities exist to greatly accelerate various operations. However, where the result requires detection of the occurrence of an event or measurement of different species present in a mixture, the detection of a signal from the medium may become the rate-limiting event.

For example, the need to be able to identify a nucleic acid sequence is increasingly important. In research, forensics, identification, as well as for other reasons, one is interested in determining the sequence of a nucleic acid. As the demand for these determinations increases, there is an increasing need for high throughput DNA analyses which provide the sequence with high fidelity. Four-color detection, one color for each nucleotide has become a mainstay of the sequencing process. For reading the colors, various excitation and detection systems have been devised. Each system must accommodate the need to accurately distinguish between background noise and signal and the different wavelengths for the different nucleotides. Furthermore, for rapid determination of the sequence of a large number of nucleic acid samples, one wishes to have numerous channels, with a different sample in each channel being sequenced simultaneously. Such systems exacerbate the problems associated with the various excitation and detection systems.

One of the systems used for nucleic acid sequencing is electrophoresis. The ability to use capillary electrophoresis has greatly improved the opportunities for high throughput sequencing. Initially, arrays of capillaries in close juxtaposition were suggested to be able to do simultaneous determinations. More recently, the opportunity to have a multiplicity of channels in a block of plastic or glass has become available. Depending on the material used for forming the channels, there can be a substantial amount of autofluorescence, which can serve to obscure the signal. In addition to autofluorescence, there is light scatter and cross-talk in the optical system to further limit the sensitivity of detection of the signal. For high throughput, the time of collection of the excitation light is limited and the number of fluorescers in the band being detected is relatively small.

While CCD (charge-coupled devices) detection has many desirable features, such as low cost, ease of use, and large areas of detection, these devices are generally thought to have low sensitivity. The ability to use these detectors where one is detecting fluorescer concentrations of 100 pM or lower at high speed in a multiplex system has been excluded There is therefore a substantial interest in developing sequencing systems using small devices comprising large numbers of channels so that multiplexed sequence determinations of a large number of samples may be simultaneously, rapidly and accurately performed.

3. Prior Art

U.S. Pat. No. 5,741,411 is an encyclopedic description of the issues associated with capillary electrophoresis and describes the use of CCD devices for detection of multichannel arrays of long capillaries for DNA sequencing. U.S. Pat. No. 5,846,708 describes a multichannel device for detecting molecular tagged targets. Methods for detecting fluorescent signals may be found in U.S. Pat. Nos. 4,820, 048; 5,543,026; 5,776,782; and 5,777,733. U.S. Pat. Nos. 5,162,022 and 5,570,015 describe capillary electrophoresis devices in which one or more channels are embodied in a single card.

SUMMARY OF THE INVENTION

Methods and devices are provided for rapid, color detection as exemplified by four-color detection in the sequencing of nucleic acids using capillary electrophoresis. The capillary electrophoresis uses a solid substrate comprising a plurality of spaced apart channels with electrodes proximal to the end of each of the channels and a separation medium in each of the channels. Each of the channels is irradiated with a single wavelength excitation light and the emission light divided into four paths by an optical train. The signal in each path is detected with an independent CCD and the signals from the CCD analyzed by a computer. The system provides for accurate resolution of the signals, with greater than 500 nucleotides capable of resolution at high speed.

BRIEF DESCRIPTION OF THE DRAWINGS

FIG. 2 is a plan view of a chip having a fan-shaped arrangement of channels with a portion as an exploded view.

DESCRIPTION OF THE SPECIFIC EMBODIMENTS

Figure 1:
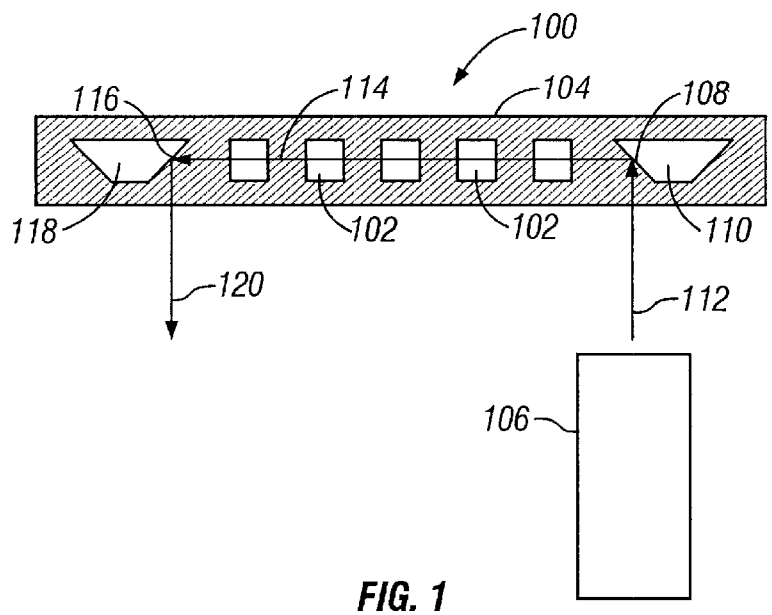
FIG. 1 is a cross-sectional view of a chip exemplifying light irradiation of the channels in the chip.

High speed color detection is provided employing an optical train for receiving light emitted from one or a plurality of channels, where the fluorescent label is moving along the channel and is irradiated at a detection site, detecting the light intensity with a CCD by binning pixels and integrating the light signal received along the channel by the pixels of the CCD. The channels are present in a microfluidic device, employing one or a plurality of channels of capillary dimensions in a solid substrate. The method finds use for rapid detection of a light signal, particularly a fluorescent signal, which is moving in a path, conveniently linear, where the molecules providing the signal are spread over a finite area, usually having a single peak. The detection method integrates the light received as the sample to be measured moves through the detection zone. The method finds particular application for nucleic acid sequencing, but may be used in any device where a transient light signal is detected and needs to be resolved at high speed, with accurate detection.

Since DNA sequencing as performed today with electrophoresis requires four color detection for high-speed throughput, DNA sequencing will be used as paradigmatic of the use of the subject invention. Since each color which is detected could be a single distinct component to be measured having the same color, one would have a simpler optical train, since the light received by the CCD would not have to be divided into different wavelengths for detection. Alternatively, as the number of entities to be determined increases, one may wish to detect more than four colors, usually not more than about eight colors, conveniently not more than about six colors.

The DNA fragments provided for the sequencing are normally provided by performing either the Sanger dideoxy method (Smith, A. J. H., Methods in Enzymology 65, 56–580 (1980) or the Maxam-Gilbert method (Gil, S. F. Aldrichimica Acta 16(3), 59–61 (1983). In each case, fluorescent dyes are provided, which may be present in the primer, in the terminating nucleotide, or may be added by reaction with a functionality which is provided as part of the extension of the primer. Various dyes and dye combinations (referred to hereinafter as "dyes" collectively) are employed, which dyes can be efficiently excited by a single light source, but will emit at different wavelengths, usually separated by at least about 10 nm, preferably separated by at least about 15 nm, and generally less than about 30 nm will be acceptable. Desirably, one can use an inexpensive laser, such as an argon laser to excite the dyes at 488 nm and/or at 514 nm, where the dyes to be excited have a significant absorption efficiency at that wavelength. Dyes of interest include xanthene dyes, e.g. fluoresceins and rhodamines, coumarins, e.g. umbelliferone, benzimide dyes, e.g. Hoechst 33258, phenanthridine dyes, e.g. Texas red, ethidium dyes, acridine dyes, cyanine dyes, such as thiazole orange, thiazole blue, Cy 5, Cyfr, carbazole dyes, phenoxazine dyes, porphyrin dyes, quinoline dyes, or the like. Thus the dyes may absorb in the ultraviolet, visible or infrared, preferably the visible wavelength range. Various combinations of dyes may be used. A common combination is: R110, R6G, ROX, and TAMRA, which has been exemplified herein, or their "d" analogs, e.g., dR110, dR6G, dROX and dTAMRA. Other combinations include: FITC, NBD chloride (4-chloro-7-nitrobenzo-2-oxa-1-diazole), TMRITC (tetramethylrhodamine isothiocyanate) and Texas Red; energy transfer combinations, such as FAM (fluorescein-5-isothiocyanate)(common donor), JOE (2',7'-dimethoxy-4', 5'-dichloro-6-carboxyfluorescein), TAMRA (N,N,N',N'-tetramethylcarboxyrhodamine), and ROX (6-carboxy-X-rhodamine) (See, U.S. Pat. No. 5,707,804); or replacing NBD chloride with NBD fluoride.

After performing the sequencing process in accordance with conventional techniques as described above, where all of the nucleotide extensions occur in a single reaction mixture or are performed in separate reaction mixtures and then combined for analysis, the mixture is introduced into the subject system. The system comprises a microfluidic device and a detector for the microfluidic device.

The microfluidic device comprises a solid substrate, referred to as a chip, having a plurality of channels of capillary dimensions and ports or reservoirs for receiving the reaction mixture. The chip may be a solid substrate having a thickness of from about 0.5 mm to 5 mm or more, although there will usually be no advantage in having a thickness of more than about 2.5 mm. A thin cover of about 0.05 to 1 mm is used to enclose the channels in the solid substrate, which cover is bonded to the solid substrate. The cover and/or the solid substrate may serve to provide the ports for access to the channels and chambers present in the device or the chambers may be extrinsic to the device and in fluid connection to the capillaries through flexible or rigid conduits. For the most part, there will be a sample reservoir and a waste reservoir at opposite sites in relation to the channel, where the reservoirs may be part of the device or connected to the channel through an external conduit. Electrodes are provided for providing an electric potential across the channel. The width of the device will vary with the number of channels present and the pattern of the channels, usually being at least 5 mm, more usually at least one centimeter and may be 10 cm or more. The spacing of the capillaries will usually be at least about 0.1 mm and not more than about 2 mm, usually not more than about 1 mm, where the spacing may be difficult to define for certain patterns for the capillary distribution. The design for the device may have parallel capillaries, fan-like capillaries, where the capillaries are spread apart at the sample entry site and the spacing narrowing at the detection site, e.g. where the capillaries define an arc of up to about 180° at the entry site and have a linear cross-section of about 50 to 200 mm at the detection site.

Normally, the cross-sectional area of the capillaries will be in the range of about 50 to 20,000 $\mu^2$, more usually from about 50 to 10,000 $\mu^2$. The length of the capillary will generally be at least about 2 cm and may be as long as 50 cm, generally being from about 2 to 40 cm. The length of the capillary will depend upon the sample being analysed, the length of the largest fragments and the number of nucleotides to be sequenced. Different materials may be used for the solid substrate, such as plastics, e.g. acrylates, exemplified by poly(methyl methacrylate), polycarbonate, poly (ethylene terephthalate), etc., silicon, silica, glass, and the like. Depending on the nature of the substrate, the surface of the channel may be coated with a polymer composition and/or a medium may be introduced into the channel. Various media have found use in capillary electrophoresis, particularly compositions that form gels or enhance the viscosity in the channel or provide a charged surface for movement by electroosmotic flow. These materials include polyacrylamide and N-substituted derivatives thereof, agarose, poly(ethylene oxide), hydroxyethylcellulose (HEC), aminoethylcellulose or other convenient separation gel or charged polymer.

The number of channels will generally range from about 1 to 2000, more usually from about 50 to 1500, frequently from about 75 to 500, in a single chip and instrumentation can be provided for reading two or more chips simultaneously. Desirably, the subject system will be able to read at least 20, more usually at least 50 and preferably at least 75 channels simultaneously with high resolution and accuracy, generally being limited to about 1000 channels for a single detector. Each of the channels will have a detection zone, where one or more windows are provided which are substantially transparent to the excitation and emission light. The windows may be a continuous window over all of the channels or an intermittent window, which covers a single channel or a plurality of channels, generally not greater than about 100. In one embodiment, the excitation light enters from the side of the channel and leaves from the other side of the channel, where the composition of the chip allows for light transmission.

The sensitivity of the system is to be able to accurately detect ($\leq 5\%$ error rate in 500 nucleotides) the individual dyes, with an exposure time for detection of less than 1 sec, usually less than about 0.5 sec, and may be as little as 100 msec or less, with a frequency of determination of at least 5 Hz and up to about 100 Hz, usually not more than about 50

Hz, frequently in the range of about 10 to 20 Hz. The concentration of the dye to be detected will usually be greater than about 5 pM, usually greater than about 10 pM and less than about 50 pM, usually less than about 40 pM. The speed and sensitivity will, to varying degrees, depend upon the dye, which is selected In performing the determination, the sample containing the extended primers will be placed in a channel directly or into a reservoir to which the channel is connected. The volume in a reservoir or chamber will generally range from about 0.1 $\mu$l to 100 $\mu$l. The volume of the sample in the channel will usually be at least about 0.5 nl, more usually at least about 1 nl, and usually not more than about 10 nl, more usually not more than about 5 nl. Different samples may be put into each channel or the same sample in a number of channels, where some redundancy is permitted, to ensure the accuracy of the sequence. Electrodes are placed at opposite ends of the channel to provide a voltage across the channel of from about 500 to 4000V to provide for separation of the sequences by their different length. Normally, the conditions of the separation and the length of the channel in which the separation occurs should allow for a spacing between oligonucleotides of from about 50 to 200 $\mu$m, which is sufficient for the optical detection employed in this invention.

The detection system involves an excitation source, optics to receive the fluorescent light, an optical train to define the area from which the light from the channel is received and to divide the light into the four different wavelength ranges for the different dyes and CCD detectors for determining the intensity of the light from the channel. These signals are then sent to a signal processor for decoding to identify the individual nucleotides.

As already indicated, the excitation source may be any source of radiation in the excitation wavelength of the dyes, coherent or non-coherent light source, and for DNA sequence analysis with the commonly used dyes, is conveniently an argon laser. Depending on the number of channels, their separation, the nature of the material of the substrate, and the separation between channels more than one light source may be used. The light may be incident to the channels, transverse to the channels, and with the appropriate configuration can provide for total internal reflection. Laser intensity would be about 750 to 2000 W/cm$^2$, using a 4 mW laser. By using the appropriate lens objectives, the light can be directed to the desired number of channels and provide the necessary intensity for excitation of the different dyes.

The light collection is dependent on minimizing background associated with light scatter, autofluorescence of the material of the chip, area of the channel covered to maximize the number of dye molecules from which light is received and the like. For example, for a 50 $\mu$m deep channel, with a 10 $\mu$m diameter beam (in air, 20×objective), at a 10 pM concentration, there will be 24 molecules in the detection region.

The subject system was demonstrated using confocal, laser-induced epifluorescence detection. Fluorescence from a DNA sequencing sample was excited by an argon ion laser (Omnichrome, 543-AP) operated at 488 nm. The laser light was directed into an inverted, epifluorescence microscope (E300, Nikon Instruments, Melville, N.Y.), passed through an excitation filter (485DF22, Omega Optical, Brattleboro, Vt.), reflected off a dichroic miror (500DRLP, Omega Optical) and focused into the channel using a 10×/0.45 NA microscope objective. The laser formed an approximately 20 $\mu$m spot within the channel which contained the DNA sample. Fluorescence was collected through the objective, passed through the dichroic mirror and a long pass filter (515EFLP, Omega Optical) and focused onto a 500 $\mu$m circular confocal aperture. The light passing through the aperture was collimated using an achromatic lens and separated into 4 colors and detected using the optical train and analysis unit 304 described in FIG. 3.

DNA sequencing was performed in a 50 $\mu$m deep by 120 $\mu$m wide channel etched into a 5-cm by 22-cm glass plate. The plate was bonded to a top glass cover plate to enclose the channels and create the bonded glass chip. The channel pattern was a cross injector comprised of an injection channel intersecting a separation channel. The effective separation length was 18 cm as measured from the channel intersection to the detection point. Each arm of the cross injector was connected to a reservoir created by a drilled hole in the top cover plate. Voltages to create electrophoretic potentials in the channels were applied using a platinum wire electrode placed in each reservoir. Reservoir voltages were controlled by computer using a 4 channel, high voltage power supply.

The DNA sequencing sample was prepared by ABI Bigdye-labeled primer ready reaction chemistry. The template used in the reaction was M13 mp18 ssDNA template standard.

The primer set is −21M13 universal primer. 2×reaction with 10 $\mu$L is carried in an ABI Thermal Cycler 2400 according to the manufacture recommendation. The thermal cycling protocol includes two phases: amplification and chasing cycles. 15 cycles of amplification are performed with a protocol of 96° C. for 10 s, 55° C. for 5 s, and 70° C. for 60 s. 15 cycles of chasing are carried with a protocol of 96° C. for 10 s and 70° C. for 60 s. Two holding cycles are followed as 96° C. for 7 min and 4° C. forever. After reaction, the reaction mixture is passed through a Centra-Sep spin column to remove the excessive salt components. 4 reactions with ddATP, ddTTP, ddGTP and ddCTP terminator and corresponding bigdye-labeled primers are preformed and pooled together. 10 $\mu$L of pooled reaction mixture are mixed with 10 $\mu$L deionized formamide and then heated up to 90° C. for 2 min. After chilling on the ice bath, the mixture is loaded onto the chips.

The sieving media is 2% LDA010 polymer solution (linear polyacrylamide) in 1×TTE buffer (50 mM Tris, 50 mM TAPS, and 2 mM EDTA with 7 M urea). The polymer solution is loaded through reservoir #3 under a pressure of 200 psi for 14 min. The separation is performed under 200 V/cm and 35° C. The temperature of the entire glass chip is controlled by a Peltier temperature controller.

The fluorescence from each channel is received by an optical fiber and transmitted to an optical train, which serves to divide the light into 4 pathways, each with a different range of wavelengths. The light may be divided by prisms, dichroic mirrors or gratings. Prism structures for wavelength separations are available from Richter Enterprises, Wayland, Mass., with a wavelength range of 430–950 nm, >80% transmission and a clear aperture of 30×8 mm. Dichroic mirrors are available from a variety of sources, e.g. Omega Optical. Filters or gratings are provided in each pathway to provide the desired wavelength signal to the CCD. While either filters or gratings may be used, for the purposes of the subject invention, filters are preferred, and may include bandpass and cutoff filters.

The light is passed through the filter and received by the CCD. Various CCDs are available from a number of sources, but the low noise, high QE CCD available from Hamamatsu has been found to be useful. Characteristics of the CCD for the subject invention are the CCD is back thinned, has 85–90% quantum efficiency, has a fast readout and can be binned along the linear direction.

A single CCD is used for each wavelength range of light to be measured. The light is focused on an area of pixels, where the signal from at least 5, usually at least 8 and not more than about 625, usually not more than about 400, preferably from about 8 to 225 pixels, more usually 8 to 144 pixels, is integrated in the area for a single channel. Generally, there will be from 2 to 25, usually 3 to 20 pixels, more usually about 9 to 100 pixels in a row and approximately the same number in a column. The signal in each row of pixels is dumped into the next row, where the number of rows in the device employed is 64. Larger or smaller numbers of rows may be used, although the minimum number of rows in a column will be at least 2 and will usually be not more than about 10. The signals from the pixels will be integrated and passed to the register, which will send the result to a computer for analysis. The detection bandwidth will generally be less than 10 Hz and more than about 0.5 Hz, usually about 1 to 5 Hz, preferably about 2 Hz. Sampling will be at a rate of at least about 5 Hz, usually at least about 10 Hz and may be as high as 50 Hz or greater. The total peak to base will usually be about 1 to 2 sec during the detection period. Sensitivity for the system was in the range of 3–7 pM.

Using the procedure described above, where the spot covered about 40–80 pixels, almost 6 to 9 rows and columns, the following results were obtained. The DNA sequencing results from the 4-CCD DNA sequencer can be described in terms of separation, speed and base calling accuracy. The resolution of two neighboring bases in an electropherogram is defined as the ratio of the mutual distance to their mean width. Most base-calling software can easily identify the peaks with resolution better than 0.5. For the DNA sequencing conducted in our 2% LDA010 polymer solution, the range of DNA fragments with separation resolution larger than 0.5 is from 50 bp to 760 bp. This ensures the 4-CCD detection system for on-chip DNA sequencing gives more than 700 bp. The fast separation requires fast data acquisition. In this system, the first peak in the electropherogram, which is the primer peak, comes out at 7.2 min; the last peak, which is the bias reptation peak, elutes out at ~26 min. All the useful information is generated from 8 min to 20 min. On the average, it is about 1.2–1.5 second per peak eluted. 10 Hz data acquisition rate of the 4-CCD detection system gives about 12 to 15 points to map out a peak, with the spot on each CCD being about 25 pixels. This is very efficient and effective to determine a Gaussian peak although it is at the low end. Higher data acquisition is desirable but not necessary to yield a better sequence result. BaseFinder software was used to call the sequence of M13mp18 sample from the raw data generated from CCD. Without any sophisticated mobility shift calibration, the base-calling accuracy for 700 bp is 95.7%. If one manually eliminates the errors caused by the mobility shift difference of the fragment sets, the sequencing accuracy is 97.8%. This demonstrates that the quality of the raw data produced from 4-CCD can be used in DNA sequencing.

For further understanding of the invention the drawings will now be considered. FIG. 1 is a diagrammatic cross-sectional view of a chip. The chip 100 has a plurality of channels 102, which are depicted as rectangular. In this design, the channels will be rectangular, although they may be elliptical or round, and conveniently for use in the subject invention will have a depth of about 25 to 100 $\mu$m and a width of about 10 to 50 $\mu$m. The channels will usually have separations greater than the width of the channel and generally in the range of about 100 to 1000 $\mu$m. A laser source 106 is directed toward an angled wall 108 of air filled channel 110 as beam 112. The beam 112 is reflected from the wall 108 by total internal reflection and is directed transversely as transverse beam 114 through the light transferring channels 102 and the separations 104 to the angled wall 116 of a second air filled channel 118 as beam 120, where it is sent to a waste light receiver, not shown. While conveniently the angle shown is 45°, which provides for orthogonal entry of the beam 112 into the channels 110, other angles could be used, where the angle of the light beam would be modified to provide the orthogonal beam. Materials, such as acrylic, can be prepared with comparatively low autofluorescence and a high efficiency of transmission, so that the chip material may be used for transmitting the beam. Other materials which may find use include glass, organic polymers, silicone, etc. Usually, the beam will be effective for from about 1 to 5 channels, more usually from about 1 to 3 channels.

Figure 2A:
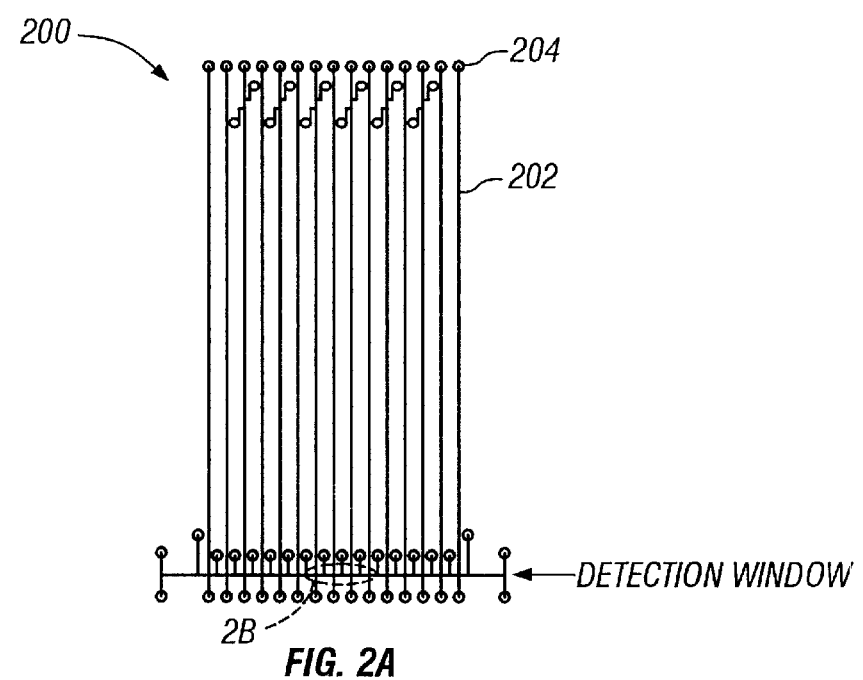
FIG. 2A is an exploded view of a portion of the chip having the ports and FIG. 2B is a cross-sectional view along line 2B of the detection region of the channels.
Figure 2B:
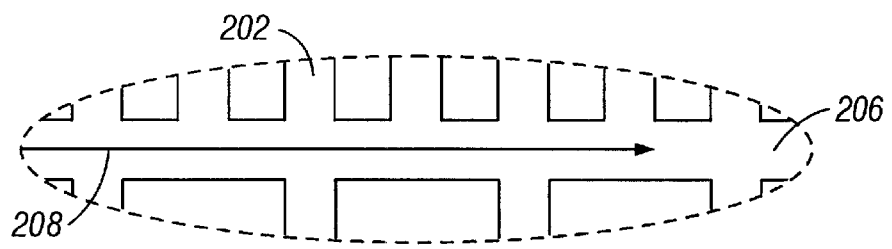

An exemplary chip is shown in FIG. 2, with exploded portions of the chip in FIG. 2A. The chip is intended to be introduced into an instrument, which would provide the sample, reagents and voltage supply for the channels. Thus the chip 200 would be inserted into a receiving opening in an instrument, where the chip would be indexed to be positioned in relation to the sample and reagent supply for each channel, as appropriate, the electrodes for each channel and the excitation light source and detector. Separate reservoirs may be provided which have the electrode for providing the voltage potential for the channels, where the reservoir is electrically connected to the channel, but may or may not have free fluidic connection with the channel. Once introduced into the instrument, the process for separation and analysis would begin automatically.

Each of the channels 202 has a separate port 204 for receiving sample and any reagents, including buffer, and as indicated, may also receive an electrode. The channels 202 are depicted as parallel, although they could be configured in a fan-like pattern and converge at the downstream side of the channel in relation to the movement of the oligonucleotides. All of the channels pass the detection window 206. Light from a laser 208 passes transversely through the channels 202 in the detection zone and fluorescent molecules are excited to emit light, which is then read by a detector.

Figure 3:
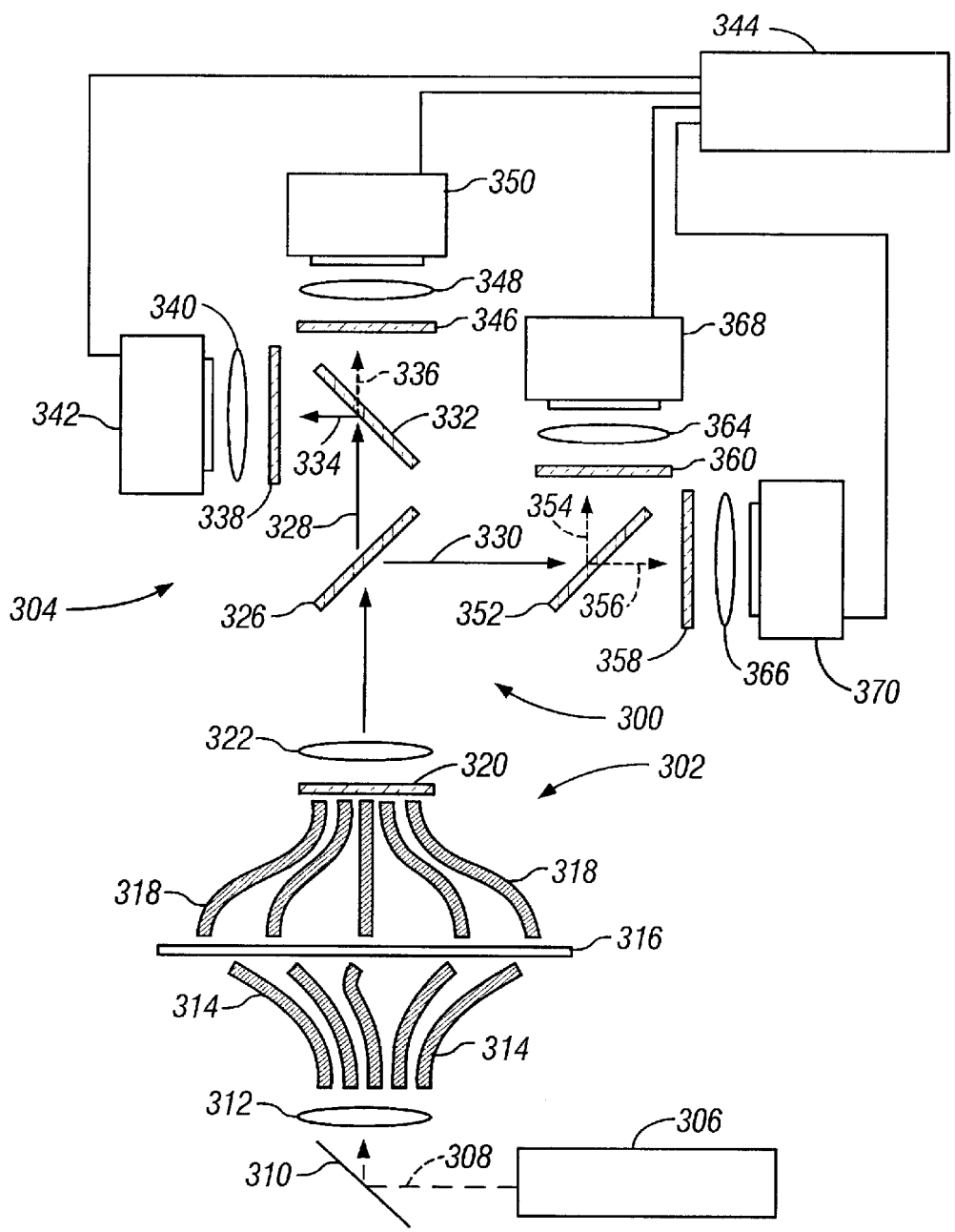
FIG. 3 is a diagrammatic view of a system according to this invention.

In FIG. 3 an exemplary system is diagrammatically shown. The system 300 has excitation and emission subunit 302 and optical train and analysis unit 304. The excitation and emission subunit 302 comprises a laser source for the excitation light. While collimated light, particularly laser light is preferred, it is not required and any light source which provides for efficient excitation of the fluorophores may be employed. While in the figure the laser 306 is shown as providing a beam 308, which is reflected by dichroic mirror 310, any arrangement may be employed which allows for efficient transmission of the light and minimizes the amount of light received in the optical train unit 304. The light beam 308 is focused by lens 312 and is then distributed by excitation optical fibers 314 to the channels of the chip 316. The chip is indexed, so as to be properly positioned in relation to the excitation optical fibers 314 and the emission optical fibers 318. Thus, each channel of the chip has a pair of optical fibers for delivering excitation light to the channel and receiving emission light from the channel.

As discussed previously, the excitation light can be provided as a beam orthogonal to the channels, where less of the excitation light will enter the emission optical fibers 318. The light from emission optical fibers 318 is filtered by filter 320 in order to cut off any stray light from the excitation light source, e.g. argon laser, where the cutoff is >515 nm. Lens 322 focuses and collimates the light from the optical fibers 318, to have the light from the individual channels in substantially parallel beams 324 for entry into the optical train 304. The optical train is shown for four color detection, but as already indicated, only a single color might need to be detected. In that case, the filter 322 could suffice to cut off light outside the wavelength range of interest, for example, a bandpass filter which would only allow light in the wavelength range of interest. One could then direct the light to a CCD camera for detection.

In FIG. 3, the optical train 304 is designed to detect four different colors, as is commonly used in DNA sequencing. The system is described for the dyes dR110, dR6G, dTAMRA and dROX. The light beams exiting from lens 322 impinge on dichroic mirror 326 and for commonly used dyes, would be divided into two beams, beam 328 and 336, which would be light above 590 nm and beam 330 and 354, which would be light below 590 nm. Beam 328 would be further divided by dichroic mirror 332 into beam 334, which would be light below 610 and beam 336, which would be light above 610. Beam 334 would be further restricted by filter 338 to a wavelength range of 590–610, focused by lens 340 and detected by CCD camera 342. The signals from CCD camera 342 would be sent to computer 344 for analysis. Similarly, beam 336 would be filtered by filter 346 to a wavelength range of 615–650, focused by lens 348 and detected by CCD camera 350. The signals from CCD camera 350 would be sent to computer 344 for analysis. In analogous fashion beam 330 would be split by dichroic mirror 352 into beams 354 and 356, passing light greater than 560 nm and reflecting light less than 560 nm. Filter 358 is a bandpass filter, which passes light of wavelength range 560–580 nm, while filter 360 is a bandpass filter which passes light in the range of 510–550. Lenses 364 and 366 focus beams 354 and 356 respectively onto CCD cameras 368 and 370, respectively. The CCD cameras 368 and 370 transmit their signals for analysis to computer 344.

Figure 4A:
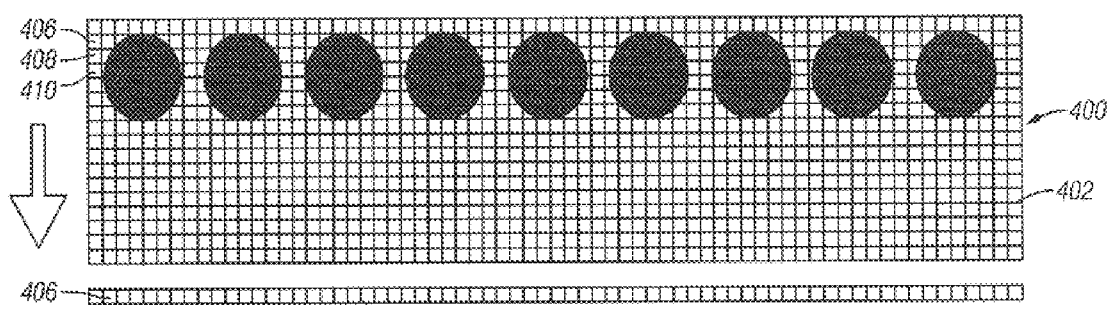
FIGS. 4A and B are diagrammatic views of the binning of the signal by the CCD.
Figure 4B:
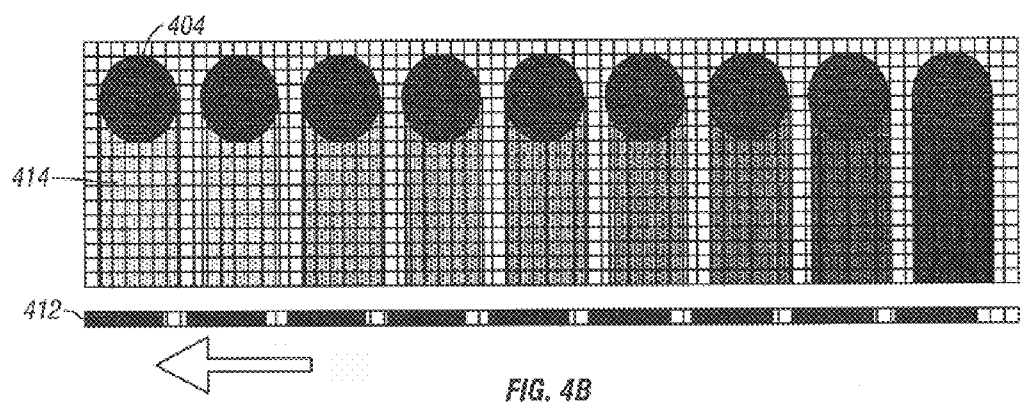

FIG. 4 is a diagrammatic view of what the CCD camera sees. In FIG. 4, each of the squares symbolizes a single pixel. In FIG. 4A the camera face 400 has a plurality of pixels which are present in columns and rows. Light from the optical fibers as depicted in FIG. 3, are focused to create a spot 404 on the camera face 400, so that light emitted from the channel impinges on the pixels and is counted by the pixels. As depicted in the figure, the diameter of the spot 404 covers about 6 pixels. The photons counted by the pixels 402 in row 406 is transferred to row 408 which is added to the photons counted in row 408 and this total is transferred to row 410 and added to the photons counted by the pixels in row 410, and so on. These counts are continuously transferred to successive rows until the total is received by register 412 and the total value sent to a data analyzer, e.g. a computer, for processing. In FIG. 4B this process is indicated by the shaded regions 414, which symbolizes the blurring of the values through the pixels and the counts are transferred from row to row and finally the total received by register 412. One may consider the method of binning as a bucket brigade, where each pixel dumps into the lower register 412 and is cleared. Charge is shifted down the column and the full charge well is always available. In this case saturation of a pixel is prevented. By binning of the pixels a more rapid and accurate detection of peaks is achieved, allowing for high throughput analysis of four colors for sequencing of DNA in a plurality of channels.

It is evident from the above description that the subject invention provides an efficient rapid way to multiplex assays and obtain a large amount of data rapidly, with high precision and with high efficiency. The methodology employs the conventional methodology for performing DNA sequencing using four color discrimination for the different nucleotides, while being able to miniaturize the methodology, so as to use very small volume samples, high rapid separation times and rapid detection times. In this way a large number of determinations may be made within a short period of time, with efficient use of the instrumentation and laboratory personnel.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. In a method for rapidly detecting light from a channel of capillary dimensions, where a plurality of individual components of a mixture comprising different fluorophores emitting different wavelengths move along said channel at spaced apart intervals for an exposure time of less than about 500 msec, where the light appears as a band, the improvement which comprises:

dividing the light from said bands into different wavelength ranges, separately detecting each wavelength range with different CCD cameras, where the light illuminates a spot which included from 2 to 100 pixels in a row and binning the signal received along the rows of pixels to provide a total for said band; and transmitting the signal to a data processor for detecting said band.

2. A method according to claim 1, wherein scanning is performed at least about 10 Hz.

3. A method according to claim 1, wherein each said CCD camera has a quantum efficiency of at least 85%.

4. A method according to claim 1 wherein said different wavelength ranges corresponding to the wavelengths of four colors.

5. A method according to claim 1 wherein said different wavelength ranges corresponding to the wavelengths of six colors.

6. A method according to claim 1 wherein said different wavelength ranges corresponding to the wavelengths of eight colors.

7. A method for performing DNA sequencing detecting four different fluorophores emitting at four different wavelengths, said method comprising:

moving electrophoretically a mixture of fluorophore-labeled oligonucleotides at a rate to provide an exposure time of less than about 500 msec to detection and at a spacing between oligonucleotides in the range of about 50 to 200 $\mu$m;

irradiating said fluorophore-labeled at a detection site with excitation light to produce bands of emitted light;

dividing the light from said bands into four different wavelength ranges; and separately detecting the light from each of said bands with different CCD cameras, where the light illuminates a spot which includes from 2 to 100 pixels in a row and binning the signal received along the rows of pixels to provide at total signal for said band.

8. A method according to claim 7, wherein said moving electrophoretically is in a channel of from about 50 to 20,000$\mu^2$ cross-section under a voltage in the range of about 500 to 4000V.

9. A method according to claim 8, wherein said channel is in a polymethylmethacrylate substrate and said channel contains linear polyacrylamide as a sieving agent.

10. A method according to claim 8, wherein said DNA sequencing is performed on at least 500 nucleotides.

11. A method according to claim 8, wherein said binning is performed by binning 8 to 36 pixels.

12. A method according to claim 8, wherein said moving comprises moving fluorophore labels dR110, dR6G, dROX and dTAMRA.

13. A method for performing DNA sequencing detecting four different fluorophores emitting at four different wavelengths, said method comprising:

moving electrophoretically, in a channel having a cross-section in the range of from about 50 to 20,000 $\mu^2$, a mixture of fluorophore-labeled oligonucleotides at a rate to provide and exposure time of less that about 500 msec to detection and at a spacing between oligonucleotides in the range of about 50 to 200 $\mu$m;

irradiating said fluorophore-labeled at a detection site with an argon laser to produce bands of emitted light;

dividing the light from said bands into four different wavelength ranges; and separately detecting the light from each of said bands with different CCD cameras, where the light illuminates a spot which includes from 2 to 100 pixels in a row and binning the signal received along the rows of pixels to provide a total signal for said band.

14. A method according to claim 13 wherein the row of pixels includes 8–64 pixels.

15. A method according to any one of claims 1, 7 or 13 wherein said dividing is accomplished by one optical element selected from the group consisting of a dichroic mirror, prism and grating.

16. A method for rapidly detecting light from a channel of capillary dimensions, where a plurality of individual components of a mixture comprising different fluorophores emitting different wavelengths move along said channel at spaced apart intervals, the method comprising:

detecting the light from said channel with more than one CCD cameras where each CCD camera detects light in a certain range and where the light illuminates a spot which includes from 2 to 100 pixels in a row and binning the signal received along the rows of pixels to provide a total signal; and transmitting the signal to a data processor.

17. The method of claim 16 said detecting includes detecting the light with four CCD cameras.

* * * * *